United States Patent [19]
Pezzuto et al.

[11] Patent Number: 5,804,575
[45] Date of Patent: Sep. 8, 1998

[54] METHODS OF MANUFACTURING BETULINIC ACID

[75] Inventors: John M. Pezzuto, River Forest; Darrick S. H. L. Kim, Chicago, both of Ill.

[73] Assignee: The Board of Trustees of the University of Illinois, Urbana, Ill.

[21] Appl. No.: 826,217

[22] Filed: Mar. 27, 1997

[51] Int. Cl.[6] .................................................. A61K 31/56
[52] U.S. Cl. ........................................... 514/169; 552/502
[58] Field of Search ............................. 514/169; 552/502

[56] References Cited

PUBLICATIONS von L. Ruzicka et al., *Helv. Chim. Acta.*, 21, 1706–1717 (1938).
Robertson et al., *J. Chem. Soc.*, 1267–1273 (1939).
Aplin et al., *J. Chem. Soc.*, 3269–3273 (1963).
Pakrashi et al., *Phytochemistry*, 7, 461–466 (1968).
Krajniak et al., *Aust. J. Chem.*, 22, 1331–1332 (1969).
Plattner et al., *J. Am. Chem. Soc.*, 94:24, 8613–8615 (1972).
Greene et al., *Protective Groups in Organic Synthesis*, John Wiley and Sons, Inc., NY, NY (1991).
Fujioka et al., *Journal of Natural Products*, 57, No. 2, 243–247 (1994).
Pisha et al., *Nature Medicine*, 1, No. 10, 1046–1051 (1995).

*Primary Examiner*—Gary Geist
*Assistant Examiner*—Deborah D. Carr
*Attorney, Agent, or Firm*—Marshall, O'Toole, Gerstein, Murray & Borun

[57] ABSTRACT

Improved methods of manufacturing betulinic acid from betulin are disclosed. The methods provide the β-isomer of betulinic acid in high purity and high yield.

19 Claims, No Drawings

METHODS OF MANUFACTURING BETULINIC ACID

FIELD OF THE INVENTION

The present invention relates to improved methods of manufacturing betulinic acid. In particular, the present invention relates to two improved methods of manufacturing the active β-isomer of betulinic acid, in high yield, from betulin.

BACKGROUND OF THE INVENTION

Betulinic acid is being intensively investigated as a potential therapeutic agent for a variety of diseases. For example, E. Pisha et al., *J. M. Nature Medicine*, 1, pages 1046–1051 (1995) discloses that betulinic acid has an unexpected selective antitumor activity against human melanoma, e.g., MEL-1, MEL-2, and MEL-4. In addition, T. Fujioka et al. *J. Nat. Prod.*, 57, pages 243–247 (1994) discloses that betulinic acid has anti-HIV activity in H9 lymphocytic cells.

Research directed to betulinic acid, and the development of betulinic acid as a therapeutic agent, has been hindered because betulinic acid presently is available in very limited quantities and at a very high cost. Betulinic acid, i.e., 3β-hydroxy-lup-20(29)-ene-28-oic acid, and betulin, however, actually exist in relatively large quantities because betulinic acid and betulin are naturally occurring compounds that can be isolated from several genera of higher plants.

For example, the bark of white birch, Betula alba, contains betulinic acid (0.025% by weight), betulin (25% by weight), and lup-20(29)-ene-3β,28-diol. Because vast quantities of white birch bark are available, betulinic acid is potentially available in large quantities. However, the methods required to isolate betulinic acid from white birch bark are tedious and laborious. Therefore, it is difficult and costly to obtain a sufficiently large sample of betulinic acid to perform an extensive testing. Accordingly, a simple synthetic route to betulinic acid is needed to provide sufficient quantities of betulinic acid to thoroughly investigate betulinic agent as a therapeutic agent, and to provide commercial quantities of betulinic acid. The present invention is directed to methods of manufacturing betulinic acid such that betulinic acid can be readily and economically available to individuals as a therapeutic agent.

SUMMARY OF THE INVENTION

The present invention, therefore, is directed to methods of manufacturing betulinic acid of sufficient purity and in sufficient yield to provide commercial quantities of betulinic acid at a commercially acceptable cost. In particular, the present invention is directed to methods of manufacturing the pharmacologically active β-isomer of betulinic acid from betulin, in high yield.

Prior publications disclose multistep synthetic routes to betulinic acid from betulin, but the multistep routes suffer from a low overall yield. For example, the synthesis of betulinic acid has been disclosed in von L. Ruzicka et al., *Helv. Chim. Acta*, 21, pages 1706–1717 (1938) and A. Robertson, *J. Chem. Soc.*, pages 1267–1273 (1939). Contrary to these prior syntheses, the present methods provide a high yield of the active β-isomer of betulinic acid from betulin via a short, simple synthetic route requiring as few as two synthetic steps.

In particular, betulin can be converted to betulinic acid in good yield using either of two different methods. In the first method, betulin first is oxidized to betulonic acid, then the betulonic acid is reduced to betulinic acid. In the second method, protecting groups are used to selectively protect the secondary alcohol (i.e., OH) functional group of betulin, and then the unprotected primary alcohol of the protected betulin is oxidized to provide the β-isomer of betulinic acid. The protecting groups are used to eliminate isomerization of the secondary alcohol group of betulin.

Each method utilizes betulin as a starting material. Betulin is a cheap and abundant starting material because betulin constitutes 25% by weight of white birch bark and is readily isolated from white birch bark. In addition, the supply of white birch bark is essentially limitless. Currently, white birch bark is an undesirable by-product of the forest industry, and large amounts of white birch bark are being burned as a waste disposal method.

DETAILED DESCRIPTION OF THE PREFERRED EMBODIMENTS

Betulinic acid, in particular the β-isomer of betulinic acid, illustrated hereafter as compound 3, was prepared in high purity and high yield from naturally occurring betulin, illustrated hereafter as compound 1, via short synthetic routes. The synthetic methods can be used to prepare commercial scale quantities of the β-isomer of betulinic acid, either for use in extensive clinical testing or as a commercial therapeutic agent.

In general, crude betulin can be isolated from white birch bark in significant quantities by extraction processes well known in the art. The extraction process uses an organic solvent, such as chloroform, methylene chloride, carbon tetrachloride, dichloroethyl ether, 1,1,1-trichlorethane, ethylene dichloride, propylene dichloride, dichloroethyl ether, similar chlorinated hydrocarbons, and mixtures thereof. The organic solvent typically has a boiling point of about 20° C. to about 100° C. to facilitate separation of the crude betulin from the solvent. A preferred extraction solvent is chloroform.

Crude betulin obtained from the extraction process is recrystallized a sufficient number of times, i.e., one to about five times, from a suitable solvent or solvent blend, like, for example, a blend of methanol and chloroform, to provide purified betulin, i.e., compound 1 of synthetic scheme 1 illustrated below.

In one embodiment of the present invention, the β-isomer of betulinic acid was prepared as follows. The purified betulin first was subjected to an oxidation reaction, such as a Jones' oxidation using chromium trioxide ($CrO_3$), sulfuric acid ($H_2SO_4$), and acetone at 0° C., to provide betulonic acid, i.e., compound 2 of scheme 1. This oxidation reaction oxidized both the primary and secondary hydroxyl (i.e., OH) functionalities to a carboxylic acid functionality and a keto functionality, respectively.

It should be understood that other oxidizing agents that convert both the primary and the secondary hydroxy functionalities of betulin to a carboxylic acid functionality and a keto functionality also can be used in the oxidation step of the synthetic method. For example, a potassium permanganate oxidation can be used. Other useful oxidizing agents include sodium dichromate in acid, chromic acid in pyridine, manganese dioxide, bromine, and a ketone in combination with a base. A preferred oxidizing agent is a combination of chromium trioxide, sulfuric acid, and acetone, i.e., a Jones' oxidation.

Scheme 1

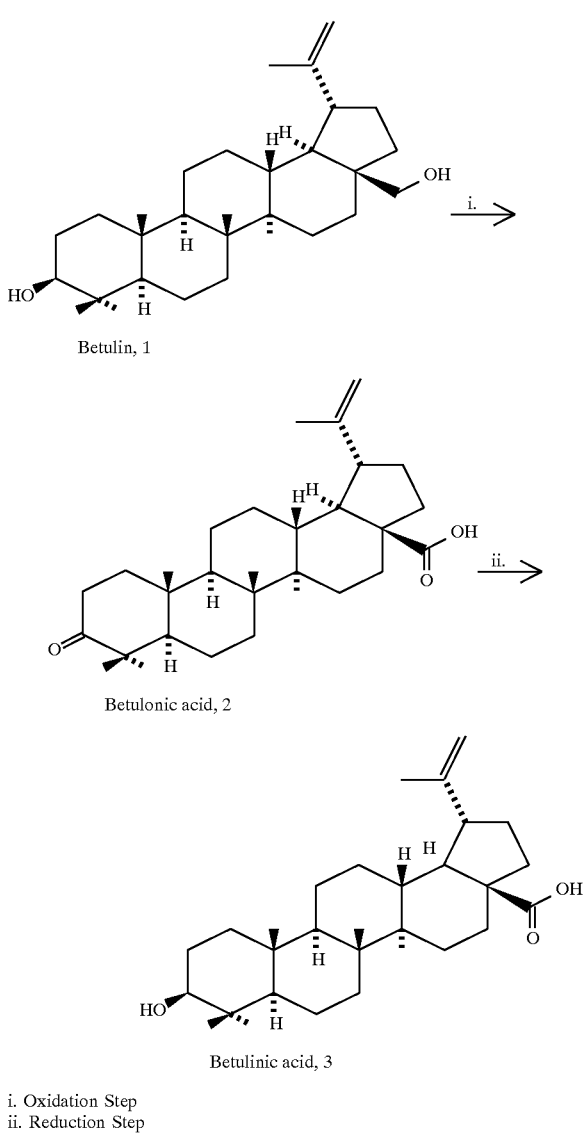

Betulin, 1

Betulonic acid, 2

Betulinic acid, 3 i. Oxidation Step
ii. Reduction Step

In synthetic scheme 1, a Jones' oxidation of betulin yielded purified betulonic acid in a 75% yield. The betulonic acid was purified and isolated by chromatographing the crude oxidation reaction product through a chromatography column containing silica gel using a blend of petroleum ether and ethyl acetate.

The betulonic acid then was reduced, using sodium boro-hydride in tetrahydroforan (NaBH$_4$/THF), for example, to provide an α- and β-isomeric mixture of betulinic acid in quantitative yield. This reduction step reduced the keto functionality of betulonic acid to a hydroxyl functionality, without reducing the carboxylic acid functionality of betulonic acid.

Therefore, in addition to a sodium boro-hydride reduction, other reducing agents that reduce a keto functionality to a hydroxyl functionality, without affecting a carboxylic acid functionality, can be used in the step of reducing betulonic acid to betulinic acid. In particular, other metallic hydrides can be used to reduce the keto functionality of betulonic acid to an alcohol functional. Exemplary reducing agents include, but are not limited to lithium borohydride; lithium tri-tert-butoxyaluminohydride, tert-butylamine, and alumina; lithium tri-ethylborohydride; tri-iso-butylaluminum hydride; and potassium tri-sec-butylborohydride. Other types of reducing agents include, for example, isopropyl alcohol in combination with aluminum isopropoxide, or diborane.

After purifying the crude reaction product of the reducing step, a proton NMR ($^1$H NMR) analysis of the reaction product showed that the ratio of the α-isomer to the β-isomer of the betulinic acid product was 5:95. The $^1$H NMR spectrum of the β-isomer was identical to the $^1$H NMR spectrum of naturally occurring betulinic acid.

The α- and β-isomeric mixture of betulinic acid was recrystallized from methanol to provide the desired β-isomer of betulinic acid as colorless needles in a 75% yield. The impure betulinic acid (i.e., an unrecrystallizable α- and β-isomeric mixture of betulinic acid) was reoxidized, and the resulting oxidation reaction product then was reduced. The resulting product of the reduction reaction was recrystallized from methanol to provide the active β-isomer of betulinic acid in a 71% overall yield. The unrecrystallizable α- and α-isomeric mixture of betulinic acid was collected for further recycling through the synthetic method of scheme 1.

The above synthetic scheme 1 provides high yields of the active β-isomer of betulinic acid, and essentially utilizes all of the betulin starting material because of the ability to recycle the α- and β-isomeric mixture of betulinic acid back through the synthetic scheme. In particular, the recyclable isomeric mixture either can be added to the next batch of betulin raw material, or simply can be recycled through the process of scheme 1 until essentially all of the betulin is converted into the β-isomer of betulinic acid. In either case, synthetic scheme 1, which provides a high yield of the β-isomer of betulinic acid, eventually uses all of the betulin raw material, thereby affording manufacturing economies and avoiding a waste disposal problem.

In another embodiment of the present invention, formation of the undesirable α-isomer of betulinic acid is completely circumvented. This synthetic approach, illustrated below as synthetic scheme 2, avoids the formation of betulonic acid, and thereby eliminates the reduction step which leads to formation of the α- and β-isomeric mixture of betulinic acid.

In synthetic scheme 2, the primary hydroxyl group of betulin first was protected as a tetrahydropyran (THP) ether, i.e., compound 4 of scheme 2, using dihydropyran, methylene chloride, and pyridinium p-toluene sulfonate (DHP/CH$_2$Cl$_2$/PPTS, 95% yield). In this reaction step, the secondary hydroxyl group of betulin was not affected. It should be noted that other commonly used protecting agents also can be used to protect the primary hydroxyl group of betulin. Numerous protecting agents for hydroxyl groups are listed in T. W. Greene et al., "Protective Groups in Organic Synthesis," John Wiley and Sons, Inc., NY, NY (1991) at pages 413–420, incorporated herein by reference. Examples of protecting groups include, but are not limited to, triphenylmethyl chloride, di-methylaminopyridine, and dimethylformamide; benzyl alcohol and potassium hydroxide; 2-methoxypropene and phosphorus oxychloride; and 2-phenoxypropene and phosphorus oxychloride.

Then, the secondary hydroxyl group of monoprotected betulin compound 4 was acetylated using acetic anhydride in pyridine (Ac$_2$O/pyridine), to yield monoprotected betulin acetate compound 5 of scheme 2 in 87% yield. Other acetylating agents also can be used. Examples of other acetylating agents include, but are not limited to, acetyl chloride; pentafluorophenyl acetate, triethylamine, and dimethylformamide; acetic anhydride, boron trifluoride etherate, and tetrahydrofuran; ketene, potassium tert-butoxide, and tetrahydrofuran; and acetic acid and trimethylsilyl chloride.

Next, the primary hydroxyl group was deprotected by selectively removing the THP ether from compound 5 using methanol and PPTS (MeOH/PPTS, 95% yield) and the resulting betulin alcohol acetate compound 6 was subjected to a Jones' oxidation (CrO$_3$/H$_2$SO$_4$/acetone) to yield the betulinic acid acetate compound 7 in 80% yield. Other compounds that can be used to remove the protecting group include, but are not limited to, formic acid and water; copper sulfate and benzene; acetic acid; acetic acid, water and tetrahydroforan; and phenyl mercaptan, trimethyl-silane, tetrabutylammonium iodide, zinc iodide, and 1,2-dichloroethane.

Finally, the acetyl group of compound 7 was removed using potassium carbonate, methanol and water (K$_2$CO$_3$/MeOH/H$_2$O) to provide the β-isomer of betulinic acid in an 88% yield. Other compounds also can be used to deacetylate compound 7, for example, but not limited to, ammonia and methanol; tributyltin methoxide and 1,2-dichlorethane; boron trifluoride etherate and wet acetonitrile; and guanidine, ethanol, and methylene chloride.

The overall yield of the β-isomer of betulinic acid from betulin starting material was about 55%. Confirmatory analysis showed that the reaction product resulting from synthetic scheme 2 was identical to the β-isomer of betulinic acid synthesized in synthetic scheme 1.

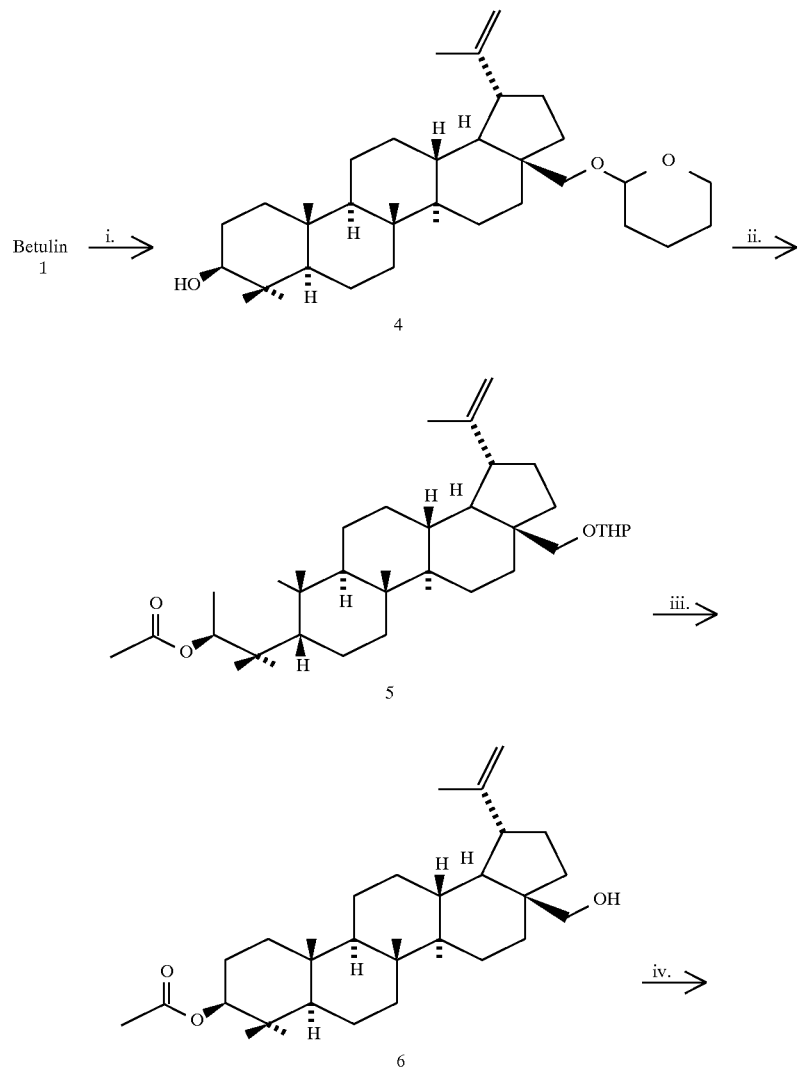

Scheme 2

-continued
Scheme 2

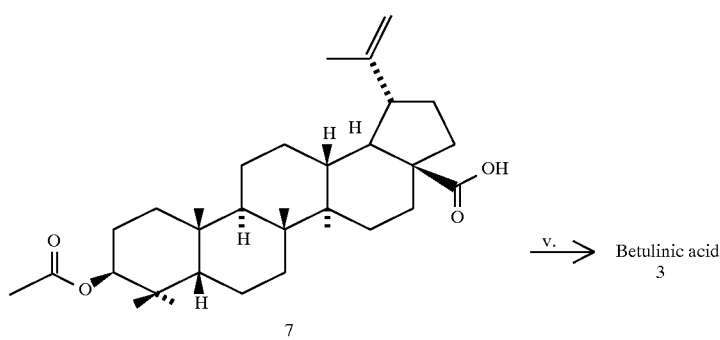

v.⟶ Betulinic acid
3

7

Reagents: (i) DHP/CH$_2$Cl$_2$/PPTS, (ii) Ac$_2$O/ pyridine, (iii) EtOH/PPTS, (iv) CrO$_3$/H$_2$SO$_4$/acetone, (v) K$_2$CO$_3$/MeOH/H$_2$O Overall, in a large-scale conversion of betulin to betulinic acid, the two-step conversion of synthetic scheme 1 is preferred, even though the α- and β-isomers of betulinic acid are generated. Synthetic scheme 1 is preferred because the synthetic method is short, the yield of the β-isomer of betulinic acid is high, and avoids waste problems. As set forth below, betulinic acid has been successfully prepared, in high yield, using both synthetic schemes 1 and 2. In particular, several 30 gram (g) scale, two-step conversions of betulin to betulinic acid, as set forth in scheme 1, have been performed successfully.

General: Melting points (mp) were determined using a Fisher-Johns apparatus and were uncorrected. CIMS was performed using a Finnigan MAT 90 instrument. $^1$H NMR and 13C NMR (carbon-13 NMR) were performed using a Varian XL-300 instrument and a standard Varian program.

Preparation of Betulonic acid (2). To a solution of betulin (1, 1.0 g, 2.26 mmol) in acetone (50 mL), cooled to 0° C., freshly prepared Jones' reagent was added dropwise. The resulting mixture was stirred for about 1.5 hours at 0° C., quenched with methanol (25 mL), stirred for an additional 5 minutes, then water (40 mL) was added. The acetone was removed under vacuum and the aqueous residue was extracted two times with 40 mL of ethyl acetate (EtOAc). The ethyl acetate layer was separated from the aqueous layer, then the ethyl acetate layer was washed first with water (20 mL) and then with brine (15 mL). The ethyl acetate layer was dried over magnesium sulfate (MgSO$_4$), then filtered, and finally the ethyl acetate was removed under vacuum. The residue was column chromatographed over silica gel (60-200 mesh) using petroleum ether/EtOAc (4:1 volume ratio) to yield 770 mg of betulonic acid, having a melting point (mp) of 247°–249° C. (literature mp 246°–2470° C.). The reaction provided a 75% yield of betulonic acid.

Preparation of Betulinic Acid (3). To THF (20 mL) containing betulonic acid (500 mg, 1.10 mmol), and cooled to 0° C., was added 440 mg, i.e., 10.0 equivalents, of sodium borohydride (NaBH$_4$). The resulting mixture was stirred at room temperature for about 10 hours. The reaction then was quenched with 3 mL of 2N aqueous hydrochloric acid (HCL), and 50% by volume of the THF was removed under vacuum. The resulting solution was diluted with EtOAc (80 mL) and was washed with water (3×5 mL) and brine (5 mL). The ethyl acetate layer was dried over MgSO$_4$, then filtered, and finally the ethyl acetate was removed under vacuum. The white residue (quantitative yield) was dissolved in hot methanol (50 mL), then the resulting solution was cooled to room temperature to induce recrystallization of 375 mg of betulinic acid, compound 1, having an mp 291°–292° C. (literature mp 290°–293° C.). The reaction provided a 75% yield of betulinic acid.

Preparation of mono-THP betulin ether (4). To a methylene chloride (CH$_2$Cl$_2$) solution (15 mL) containing betulin (2, 450 mg, 1.016 mmol) was added dihydropyran (DHP, 94 mg, 1.12 mmol) and pyridinium p-toluene sulfonate (PPTS, 30 mg. 0.12 mmol) at room temperature and under a nitrogen (N$_2$) blanket. The resulting mixture was stirred for three days. After completion of the reaction, 5 mL of saturated sodium bicarbonate (NaHCO$_3$) was added to the reaction mixture. The organic layer was separated from the aqueous layer, next was washed with a saturated sodium chloride (NaCl) solution (5 mL), then dried over MgSO$_4$, filtered, and finally the methylene chloride was removed under vacuum. The residue was chromatographed over silica gel using petroleum ether/EtOAc (4:1 volume ratio) to provide the mono-THP ether of betulin, i.e., compound 4, as a diastereomeric mixture (508 mg, 95%). The diastereomeric mixture 4 was subjected to a subsequent reaction without separation and isolation of isomers. A mass spectrum of the reaction product gave MS (CI) m/e (rel intensity) 441 (-THP, 10), 425 (-OTHP, 100), 407 (-OTHP-H$_2$O, 12).

Preparation of mono-THP ether betulin acetate (5). To 8 mL of a pyridine solution containing the diastereomeric mixture of mono-THP betulin ether 4 (280 mg, 0.53 mmol) was added acetic anhydride (110 mg, excess). The resulting mixture was stirred for about 36 hours at room temperature. The pyridine then was removed under vacuum, and the residue was diluted with EtOAc (40 mL) and washed with water (2×5 mL) and saturated NaCl (5 mL). The organic layer was separated from the aqueous layer, dried over MgSO$_4$, then filtered, and finally the EtOAc was removed under vacuum. The residue was chromatographed over silica gel using petroleum ether/EtOAc (4:1 volume ratio) to give a diasteromeric mixture of mono-THP ether betulin acetate, i.e., compound 5, in 87% yield (263 mg). The diastereomeric mixture 5 was subjected to a subsequent reaction without separation and isolation of isomers. A mass spectrum of the reaction product gave MS (CI) m/e (rel intensity) 569 (M+H$^+$, 8) , 509 (—CH$_3$COOH, 26), 485 (-THP, 12), 468 (-OTHP, 10), 425 (—CH$_3$COOH-THP, 100), 409 (—CH$_3$COOH-OTHP, 8), 407 (17).

Preparation of betulin acetate alcohol (6). To a 5 mL methanol solution containing the diastereomeric mixture of mono-THP ether betulin acetate 5 (260 mg, 0.457 mmol) was added PPTS (10 mg, 0.04 mmol). The resulting mixture was stirred for about 36 hours at room temperature. The reaction solution then was quenched with saturated $NaHCO_3$ (5 mL), and extracted with EtOAc (50 mL). The organic layer from the aqueous layer was separated, and washed with water (2×100 mL), then dried over $MgSO_4$, filtered, and finally EToAc was removed under vacuum. The residue was chromatographed over silica gel using petroleum ether/EtOAc (4:1 volume ratio) to afford the betulin acetate alcohol, i.e., compared to 6, in 95% yield (210 mg). The compound had an mp 258°–259°C. (literature mp 259–260); $^{13}C$ NMR (75.5 MHz, $CDCl_3$), δ171.04, 150.45, 109.72, 80.91, 60.52, 55.34, 50.27, 48.77, 47.79, 47.76, 42.68, 40.90, 38.35, 37.77, 37.26, 37.05, 34.13, 33.95, 29.70, 29.12, 27.92, 27.00, 25.13, 23.67, 21.34, 20.81, 19.04, 18.16, 16.48, 16.16, 15.95, 14.70; and an MS (CI) m/e (rel intensity) 485 ($M+H^+$, 4), 467 (—H2O, 27), 425 (—$CH_3COOH$, 100), 407 (22).

Preparation of betulinic acid acetate (7).

Freshly prepared Jones' reagent (1.0 mL) was added dropwise, at 0° C., with stirring, to an acetone (10 mL) solution containing betulin acetate alcohol compound 6, (170 mg, 0.35 mmol). The resulting mixture was stirred at 0° C. for about 1.5 hours, then was quenched with methanol (5 mL). After stirring for 5 minutes, water (7 mL) was added to the mixture. The organic solvents were removed under vacuum and the aqueous residue was extracted with EtOAc (2×10 mL). The organic layer was separated from the aqueous layer, then washed with water (2×5 mL) and saturated NaCl (5 mL). The organic layer was dried over $MgSO_4$, then filtered, and finally the EtOAc was removed under vacuum. The residue was chromatographed over silica gel using petroleum ether/EtOAc (4:1 volume ratio) to provide betulinic acid acetate compound 7 in 80% yield (140 mg), having an mp 288°–290° C. (literature mp 289°–291° C.); a $^{13}C$ NMR (75.5 MHz, $CDCl_3$) δ182.12, 171.08, 150.36, 109.74, 80.93, 56.38, 55.38, 50.36, 49.22, 46.93, 42.39, 40.66, 38.39, 38.36, 37.78, 37.09, 37.04, 34.20, 32.13, 30.54, 29.67, 27.93, 25.41, 23.68, 21.33, 20.82, 19.33, 18.14, 16.46, 16.17, 16.02, 14.64; and an MS (CI) m/e (rel intensity) 499 ($M+H^+$, 43), 453 (—$CO_2H_2$, 21), 439 (—$CH_3COOH$, 100).

Removal of the acetyl group. Betulinic acid acetate compound 7 (80 mg. 0.16 mmol) was stirred in aqueous methanol solution containing excess potassium carbonate ($K_2CO_3$) for about 24 hours to provide betulinic acid, compound 3, in 88% yield after column chromatography (petroleum ether/EtOAc, 4:1 volume ratio), having an mp 291°–292° C. (literature mp 290°–293° C.).

What is claimed is:

1. A method of manufacturing betulinic acid comprising the steps of:
   (a) subjecting betulin to an oxidation reaction to provide a reaction product wherein a primary alcohol functionality of betulin is converted to a carboxylic acid functionality and a secondary alcohol functionality of betulin is converted to a keto functionality;
   (b) subjecting the reaction product of step (a) to a reduction reaction to convert the keto functionality to a secondary alcohol functionality and thereby form a reaction mixture containing an α-isomer of betulinic acid and a β-isomer of betulinic acid;
   (c) separating the β-isomer of betulinic acid from the reaction mixture of step (b) to provide the β-isomer of betulinic acid; and
   (d) purifying the β-isomer of betulinic acid.

2. The method of claim 1 wherein the betulin is oxidized in step (a) using an oxidizing agent selected from the group consisting of chromium trioxide, sulfuric acid, and acetone; potassium permanganate; sodium dichromate in an acid; chromic acid in pyridine; manganese dioxide; bromine; and a ketone in combination with a base.

3. The method of claim 1 wherein the betulin is oxidized in step (a) using chrominum trioxide, sulfuric acid, and acetone at 0° C.

4. The method of claim 1 wherein the reaction product of step (a) is isolated in at least a 75% yield.

5. The method of claim 1 wherein the reaction product of step (a) is reduced in step (b) using a reducing agent capable of reducing a keto functionality to a secondary alcohol functionality, wherein said reducing agent lacks an ability to reduce a carboxylic acid functionality.

6. The method of claim 1 wherein the reaction product of step (a) is reduced in step (b) using a reducing agent selected from the group consisting of sodium borohydride; diborane; isopropyl alcohol and aluminum isopropoxide; lithium borohydride; lithium tri-tert-butoxyaluminohydride, tert-butylamine, and alumina; lithium triethylborohydride; tri-iso-butylaluminum hydride; and potassium tri-sec-butylborohydride.

7. The method of claim 1 wherein the reaction product of step (a) is reduced in step (b) using sodium borohydride.

8. The method of claim 1 wherein the reaction mixture of step (b) is isolated in at least a 75% yield.

9. The method of claim 1 wherein the β-isomer of betulinic acid is isolated in at least an overall 60% yield from the betulin.

10. The method of claim 1 further comprising the step is subjecting the α-isomer of betulinic acid generated in step (b) to an oxidation reaction to regenerate the reaction product of step (a).

11. The method of claim 10 further comprising the steps of subjecting the regenerated reaction product of step (a) to form a regenerated mixture of the α-isomer and the β-isomer of betulinic acid, then separating the β-isomer from the α-isomer to provide the β-isomer of betulinic acid.

12. A method of manufacturing betulinic acid comprising the steps of:
   (a) reacting betulin with a protecting compound capable of reacting with a primary hydroxyl group of betulin, wherein the protecting compound lacks an ability to react with a secondary hydroxyl group of betulin, to form protected betulin;
   (b) reacting the protected betulin of step (a) with an acetylating compound to yield an acetylated and protected betulin;
   (c) reacting the acetylated and protected betulin of step (b) with a compound capable of removing the protecting compound to generate an acetylated betulin;
   (d) subjecting the acetylated betulin of step (c) to an oxidation reaction to generate a betulinic acid acetate; and
   (e) removing the acetyl group from the betulinic acid acetate of step (d) to provide the β-isomer of betulinic acid.

13. The method of claim 12 wherein the protecting compound is selected from the group consisting of dihydropyran and pyridinium p-toluene sulfonate in methylene chloride; triphenylmethyl chloride, dimethylaminopyridine, and dimetnylform-amide; benzyl alcohol and potassium hydroxide; 2-methoxypropene and phosphorus oxychloride; and 2-phenoxypropene and phosphorus oxychloride.

14. The method of claim 12 wherein the acetylating compound is selected from the group consisting of acetic anhydride in pyridine; acetyl chloride; pentafluorophenyl acetate, triethylamine, and dimethylformamide; acetic anhydride, boron tri-fluoride etherate, and tetrahydrofuran; ketene, potassium tert-butoxide, and tetrahydrofuran; and acetic acid and trimethylsilyl chloride.

15. The method of claim 12 wherein the protecting group is removed in step (c) using a compound selected from the group consisting of pyridinium p-toluene sulfonate; formic acid and water; copper sulfate and benzene; acetic acid; acetic acid, water and tetrahydroforan; and phenyl mercaptan, trimethylsilane, tetrabutylammonium iodide, zinc iodide, and 1,2-dichloroethane.

16. The method of claim 12 wherein the oxidation reaction of step (d) is performed using an oxidizing agent selected from the group consisting of chromium trioxide, sulfuric acid, and acetone; potassium permanganate; sodium dichromate in an acid; chromic acid in pyridine; manganese dioxide; bromine; and a ketone in combination with a base.

17. The method of claim 16 wherein the oxidation reaction of step (d) is performed using chrominum trioxide, sulfuric acid, and acetone at 0° C.

18. The method of claim 12 wherein the acetyl group is removed using a reagent selected from the group consisting of potassium, carbonate, methanol, and water; ammonia and methanol; tributyltin methoxide and 1,2-dichloroethane; boron trifluoride etherate and wet acetonitrile; and guanidine, ethanol, and methylene chloride.

19. The method of claim 12 wherein the overall yield of the α-isomer of betulinic acid from betulin is greater than 50%.

* * * * *

UNITED STATES PATENT AND TRADEMARK OFFICE
CERTIFICATE OF CORRECTION

PATENT NO.    : 5,804,575
DATED         : September 8, 1998
INVENTOR(S)   : Pezzuto et al.

It is certified that error appears in the above-identified patent and that said Letters Patent is hereby corrected as shown below:

```
Column 3, line 59, "boro-hydride" should be
-- borohydride --

Column 7, line 35, "13C" should be -- ¹³C --

Column 9, line 18, "(-H2O," should be -- (-H₂O, --
```

Signed and Sealed this

Sixteenth Day of November, 1999

Attest:

Q. TODD DICKINSON

*Attesting Officer*    *Acting Commissioner of Patents and Trademarks*